United States Patent [19]

Andrew

[11] Patent Number: 5,599,186
[45] Date of Patent: Feb. 4, 1997

[54] IMPLEMENT FOR EXTRACTING DENTAL BRIDGES AND THE LIKE

[75] Inventor: Vladimir Andrew, Strasbourg, France

[73] Assignee: Anthogyr, Société Anonyme, Sallanches, France

[21] Appl. No.: 418,059

[22] Filed: Apr. 6, 1995

[51] Int. Cl.[6] ............................. A61C 5/00; A61C 3/00
[52] U.S. Cl. .................... 433/215; 433/153; 433/159; 433/157
[58] Field of Search ................................. 433/153, 154, 433/157, 158, 159, 161, 215

[56] References Cited

U.S. PATENT DOCUMENTS

| | | | |
|---|---|---|---|
| 3,377,704 | 4/1968 | Brodie et al. | 32/43 |
| 3,579,834 | 5/1971 | Reed, Jr. | 433/154 |
| 3,834,026 | 9/1974 | Klein | 32/43 |
| 4,197,647 | 4/1980 | Goldenthal | 433/159 |
| 4,417,876 | 11/1983 | Lynch | 433/161 |
| 4,474,500 | 10/1984 | Lynch | 433/161 |
| 5,015,185 | 5/1991 | Cane et al. | 433/153 |
| 5,197,877 | 3/1993 | Andrew | 433/153 |

FOREIGN PATENT DOCUMENTS

| | | |
|---|---|---|
| 3406514 | 9/1985 | Germany . |
| 8810805 | 12/1988 | Germany . |
| 3808880 | 9/1989 | Germany . |
| 831750 | 3/1960 | United Kingdom . |

*Primary Examiner*—Nicholas D. Lucchesi
*Attorney, Agent, or Firm*—Panitch Schwarze Jacobs & Nadel, P.C.

[57] ABSTRACT

An implement for extraction of bridges from the mouth of dental patients has a flexible wire engageable with a bridge at a distance from the edge of the bridge and at a distance from the gums of the patient, and a force applying unit which can pull the wire in a direction to lift the bridge off the respective teeth. The wire can engage the connector or connectors between neighboring crowns of a bridge and then be locked in the force applying unit.

12 Claims, 2 Drawing Sheets

5,599,186

IMPLEMENT FOR EXTRACTING DENTAL BRIDGES AND THE LIKE

FIELD OF THE INVENTION

The invention relates to implements or instruments for extracting bridges and/or other dental restorations or prostheses from the mouths of dental patients.

BACKGROUND OF THE INVENTION

Extraction of bridges, crowns and similar prostheses is a task which must be carried out by a physician or by a skilled technician. The implements which are presently available for the performance of such tasks are not entirely satisfactory.

U.S. Pat. No. 5,197,877 (published Mar. 30, 1993) discloses a looped wire the ends of which are held in a housing and which is to be placed around a connection between two joined crowns of a bridge. The housing carries a guide for a reciprocable hammer which is caused to repeatedly strike an anvil in order to loosen the bridge preparatory to complete extraction from the mouth of a wearer. The implement of the U.S. Patent exhibits the drawback that it is possible to place the wire around only one connection between two crowns of a bridge. Consequently, the bridge is lifted on one side only and can be damaged easily.

OBJECTS OF THE INVENTION

An object of the invention is to provide a simple, compact and inexpensive implement for extraction of prostheses (such as bridges) from the mouth of a patient.

Another object of the invention is to provide an implement which is less likely to damage a prosthesis than heretofore known implements.

An additional object of the invention is to provide an implement which is constructed, assembled and can be used in such a way that it is less likely to change the orientation of a prosthesis during extraction from the mouth of a patient.

Still another object of the invention is to provide an implement which is designed to simultaneously engage a prosthesis at a plurality of different locations.

An additional object of the invention is to provide a novel and improved method of extracting bridges or other types of dental prostheses or dental restorations from the mouths of the wearers without the risk of injury, infection and/or damage to the prosthesis and/or bonding material.

A further object of the invention is to provide a method which facilitates rapid and painless extraction of prostheses.

Still another object of the invention is to provide an implement or instrument which is simple to use and easy to take apart for the purposes of cleaning, inspection or modification.

A further object of the invention is to provide an implement which can be manipulated to extract a bridge in such a way that the extracted part can be reinserted without the need for any repair work attributable to extraction from the mouth of the patient.

SUMMARY OF THE INVENTION

The invention resides in the provision of an implement or instrument for extracting dental prostheses (e.g., damaged bridges) of the type affixed to at least two teeth and having at least one portion which is spaced apart from the gums of the wearer of the prosthesis.

The implement can include an elongated flexible element having a first end and a second end, and the force applying means of such implement preferably comprises a housing having means for anchoring the ends of the flexible element therein subsequent to looping of the flexible element around the at least one portion of a prosthesis to be extracted, e.g., around the aforementioned bonded connections between two or more neighboring crowns. The ends of the flexible element can include or constitute heads, and the anchoring means can include two spaced-apart sockets which are provided in the housing, one for each end of the flexible element and each having an enlarged portion for the respective head. The anchoring means can further comprise means for releasably confining at least one of the heads in the enlarged portion of the respective socket. Such confining means can comprise a screw or another threaded member which mates with the housing and prevents extraction of the one head from the enlarged portion of the respective socket.

Alternatively, the confining means can comprise a closure (e.g., a lever, a washer or the like) which overlies the enlarged portion of at least one of the sockets. The housing can further comprise a hole through which the flexible element can be looped at least once.

The flexible element can include a length of metallic wire having a first diameter which is slightly smaller than the diameters of holes or bores which are provided in the housing and each of which forms part of one of the sockets. The diameter of at least one of the heads can exceed the diameter of a hole or bore.

The second unit can further comprise means (such as a standard dentist's tool with a handle and a hook at one end or at each end of the handle) for pulling the housing. To this end, the housing preferably comprises at least one edge (e.g. a recess and/or a yoke) which is engageable by the pulling means.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. Individual features of the embodiment of the invention may be used alone or all together.

DETAILED DESCRIPTION OF PREFERRED EMBODIMENT

Figure 1:
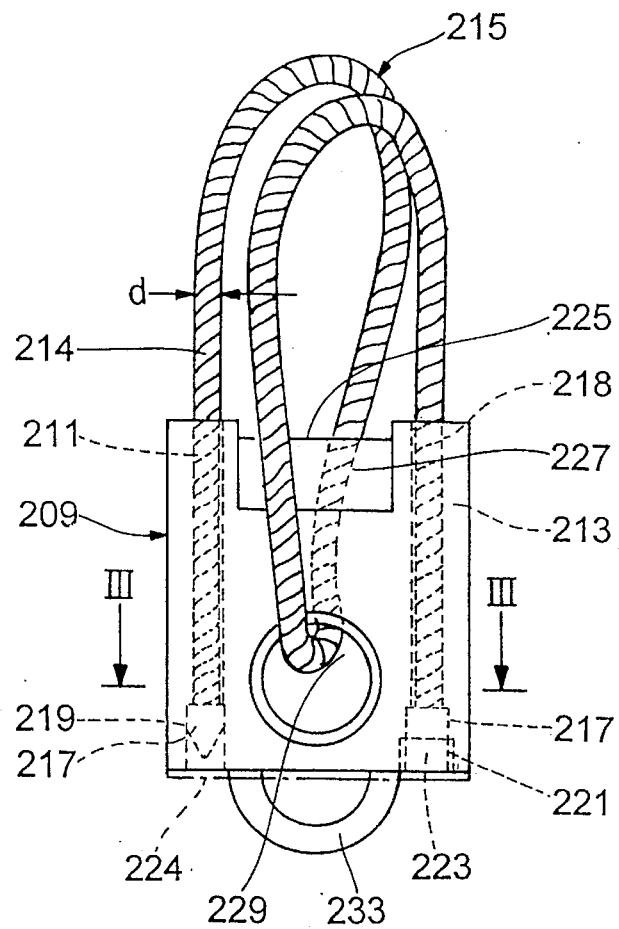
FIG. 1 is a side elevational view of an implement which can be used for the extraction of bridges and wherein the first unit comprises an elongated flexible element.
Figure 2:
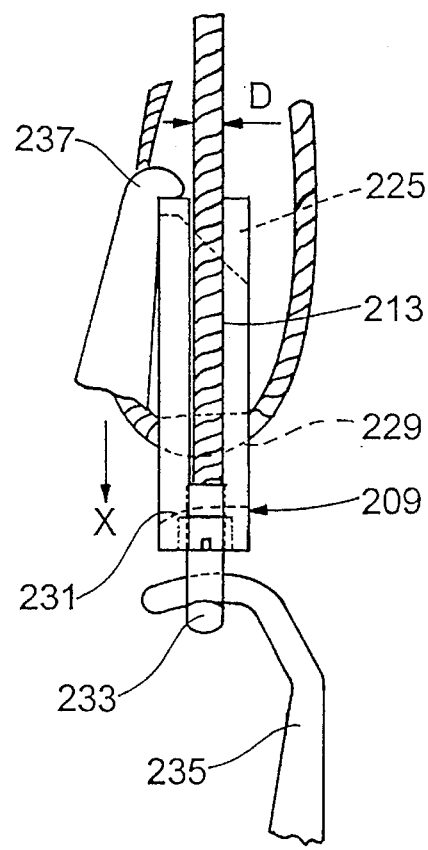
FIG. 2 is an end elevational view of the implement of FIG. 1, and further showing two hook-shaped devices which can be used to exert a pull in a direction to extract a bridge from the mouth of the wearer.
Figure 3:
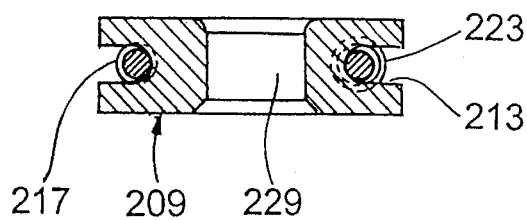
FIG. 3 is a top sectional view substantially as seen in the direction of arrows from the line III—III of FIG. 1.

The extracting element shown in FIGS. 1 to 3 comprises as a first unit a piece of wire 214 (preferably consisting of numerous metallic filaments, particularly steel filaments) with two ends which are provided with enlarged heads 217. The second unit of the implement of FIGS. 1 to 3 comprises a substantially flat rectangular or square housing or casing 209 having two lateral sockets each of which includes an elongated hole or bore 211, an elongated open slot 213 which extends from the respective hole 211 to the external surface of the housing 209, and an enlarged portion 219 for a head 217 of the flexible extracting element 215. The holes 211 are preferably parallel or nearly parallel to each other, and their diameters D are slightly larger than the diameter d of the wire 214 of the flexible element 215 but at least slightly smaller than the diameters of the enlarged portions 219.

The enlarged heads 217 can be obtained by soldering, welding, press fitting or otherwise securing suitable sleeves or caps to the ends of the flexible element 215. The diameters of the heads 217 are selected in such a way that they fit snugly into the respective enlarged portions 219 while the adjacent portions or extremities 218 of the flexible element 215 are received in the holes 211 of the respective sockets.

The width of the narrowest portions of the slots 213 (at the respective holes 211) can at least match the diameter d of the wire 214 of the flexible element 215 so that the extremities 218 of this element can be readily inserted into and withdrawn from the sockets in directions from the left and from the right, as seen in FIG. 1.

One of the heads 217 can be more or less permanently anchored in the housing 209. This can be seen in the right-hand portion of FIG. 1 where the enlarged portion 219 is tapped, as at 221, to accept the shank of a threaded fastener 223 serving to preferably releasably capture or confine the right-hand head 217 in the enlarged portion 219 of the respective socket. In addition to or in lieu of the fastener 223, the means for confining one of the heads 217 or both heads 217 in the enlarged portions 219 of the respective sockets can comprise a cover, closure or lid 224 (indicated in FIG. 1 by broken lines) pivotable to and from an operative position in which it overlies the adjacent ends of the sockets. It is also possible to employ a cover 224 having two arms one of which can be pivoted to and from a position of overlap with the right-hand head 217 and the other of which can be pivoted to and from a position of overlap with the left-hand head 217. The cover 224 can be provided with an opening or with two openings, each in register with one of the holes 211.

Figure 4:
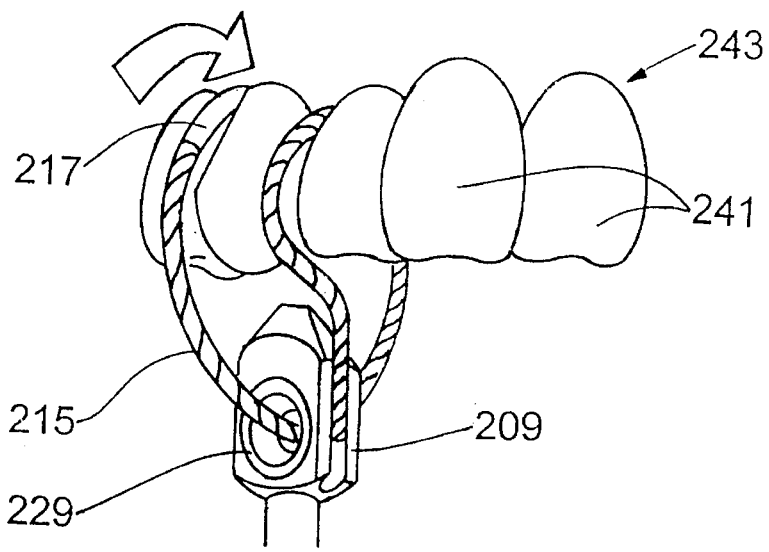
FIG. 4 is a perspective view of a portion of an implement wherein the flexible element is twice partly looped around.
Figure 5:
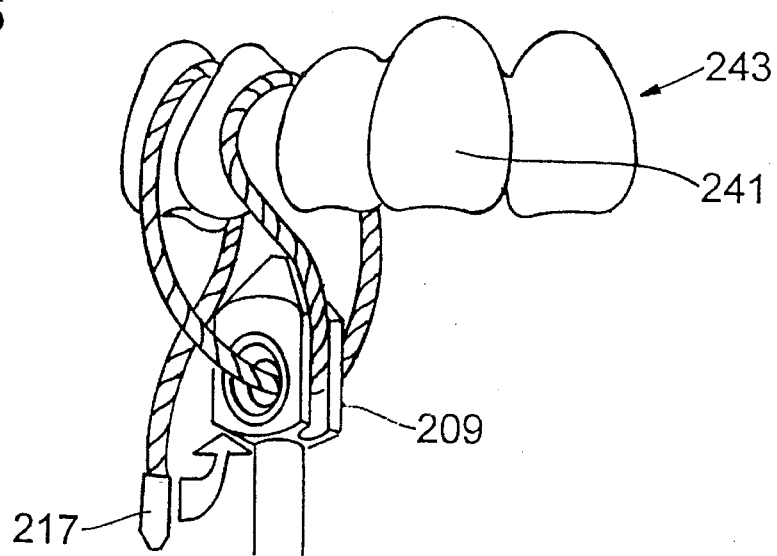
FIG. 5 is a perspective view of a portion of the implement wherein the flexible element is ready to be fastened at the housing.
Figure 6:
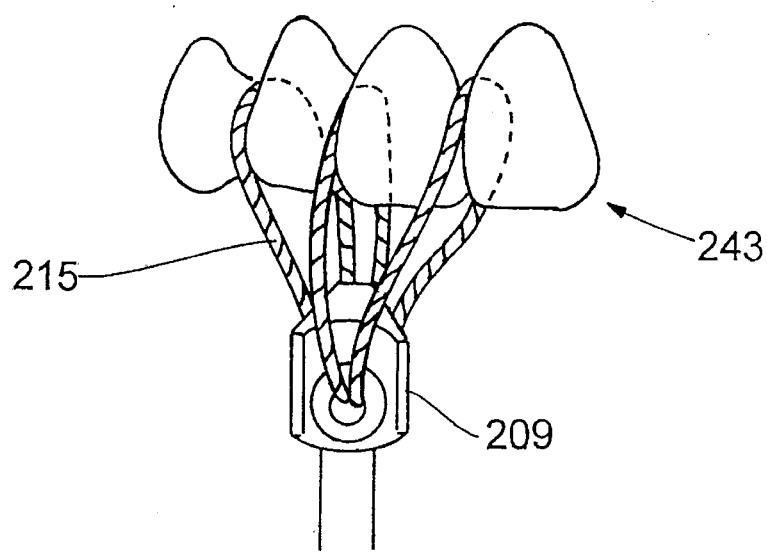
FIG. 6 is a perspective view of a portion of an implement with a flexible element three times looped.

The housing 209 is provided with a recess 225 which is located between the sockets (and more specifically between the holes 211 in the housing), with a through hole or opening 229 adjacent the enlarged portions 219 of the sockets, and/or with a yoke 233. The purpose of the recess 225 and/or yoke 233 is to permit engagement with a customary dentist's tool 235 (e.g., a hook at one end of a handle) or another dentist's tool 237, namely a stepped tool with a pallet at one end. Such tool or tools are used to exert a pull upon housing 209 in a downward direction x, as viewed in FIGS. 1 and 2. The recess 225 is preferably bounded in part by an inclined bottom surface 227, and the opening 229 can be bounded in part by an inclined bottom surface 231. The purpose of the hole 229 is to permit passing through at least once the flexible element 215 before fitting the head 217 into the enlarged portion 219. The operation of the implement of FIGS. 1 to 3 is as follows:

The fastener 223 is applied to secure the right-hand head 217 of FIG. 1 in the enlarged portion 219 of the respective socket. The left-hand head 217 is not confined in the housing 209 and can be caused to pass between the patient's gums and a connector of the bridge including the crowns of the bridge 243 (FIG. 4). The flexible element 215 is then looped, and passed through hole 229 and again caused to pass between a neighbouring connector, and its exposed extremity 218 is introduced into the still unoccupied hole 211 so that the head 217 enters the enlarged portion 219 of the left-hand socket in the housing 209 of FIGS. 1 and 5.

The surface bounding the recess 225 and/or the yoke 233 is then engaged by a tool 235 and/or 237 to exert a pull in the direction of arrow X and to thus exert a pull upon the connector which is engaged by the bight of the looped flexible element 215 while the two heads 217 of the element 215 are securely anchored in the enlarged portions 219 of the respective sockets. If the dentist realizes that the engagement of the housing 209 by a tool 235 or 237 at the recess 225 is not very convenient or not the most satisfactory way of exerting a pull upon the looped flexible element 215, the dentist causes the tool to engage the surface bounding the opening 229 or to engage the yoke 233. Thus, the dentist has the option of selecting the application of a pulling force in a manner which is most convenient to the dentist and which ensures most convenient and painless extraction of a bridge. The extremities 218 of the flexible element 215 can be dimensioned in such a way that they must be forced from the respective slots 213 into the adjacent holes 211. This greatly reduces the likelihood of accidental removal of such extremities from the respective sockets prior to tightening of the flexible element 215, i.e., prior to start of the actual extracting operation.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An implement or extracting dental prostheses of a type affixed to at least two teeth and having at least one portion spaced apart from the gums of a wearer, comprising a first unit including an elongated flexible element having a first end and a second end, and a second unit including means for applying to said at least one portion a force in a direction away from the gums of the wearer to thereby separate the prosthesis from the at least two teeth, said force applying means comprising a housing having means for anchoring said ends therein subsequent to looping of said flexible element around the at least one portion of the prosthesis to be extracted, said housing having an opening therethrough, said opening being sufficiently large to permit the flexible element to pass through the opening at least once after looping around a portion of the prosthesis and before anchoring in said anchoring means.

2. The implement of claim 1, wherein said ends include heads and said anchoring means includes two spaced apart sockets provided in said housing, one socket for each of said ends and each socket having an enlarged portion for receiving the respective head.

3. The implement of claim 2, wherein said anchoring means further comprises means for releasably confining at least one of said heads in the enlarged portion of the respective socket.

4. The implement of claim 3, wherein said confining means comprises a threaded member mating with said housing.

5. The implement of claim 3, wherein said confining means comprises a closure which overlies the enlarged portion of at least one of said sockets.

6. The implement of claim 5, wherein said flexible element has a first diameter and each of said sockets includes a hole having a second diameter slightly greater than said first diameter.

7. The implement of claim 6, wherein at least one of said heads has a diameter greater than said second diameter.

8. The implement of claim 7, wherein said housing further includes at least one edge which is engageable by a pulling device.

9. The implement of claim 8, wherein said at least one edge of said housing is selected from the group consisting of a recess, a hole and a yoke.

10. The implement of claim 1, wherein said housing includes means for passing through said flexible element.

11. A method for extracting dental prostheses of a type affixed to at least two teeth and having at least one portion spaced apart from the gums of a wearer, employing the implement of claim 1, comprising passing the first end of said flexible element between said at least one portion of the prosthesis and the gums of the wearer while holding the second end stationary, passing the flexible element through said opening to form a loop, passing the first end of said flexible element between a second portion of the prosthesis and the gums of the wearer, and anchoring the flexible element in the anchoring means to form a second loop.

12. The method according to claim 11, wherein the flexible element is looped around at least three portions of the dental prosthesis and passes through said opening at least twice.

* * * * *